(12) United States Patent
Lippert (10) Patent No.: US 8,399,857 B2
(45) Date of Patent: Mar. 19, 2013

(54) LUMINESCENCE MICROSCOPY WITH ENHANCED RESOLUTION

(75) Inventor: Helmut Lippert, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 13/342,370

(22) Filed: Jan. 3, 2012

(65) Prior Publication Data

US 2012/0097865 A1 Apr. 26, 2012

Related U.S. Application Data

(63) Continuation of application No. 12/442,093, filed as application No. PCT/EP2007/007882 on Sep. 10, 2007.

(30) Foreign Application Priority Data

Sep. 29, 2006 (DE) .......................... 10 2006 046369

(51) Int. Cl.
*G01N 21/64* (2006.01)

(52) U.S. Cl. .................................................. 250/461.1

(58) Field of Classification Search ............... 250/461.1, 250/458.1, 459.1
See application file for complete search history.

(56) References Cited

U.S. PATENT DOCUMENTS

| | | | |
|---|---|---|---|
| 5,814,820 A | 9/1998 | Dong et al. | |
| 5,866,911 A * | 2/1999 | Baer | 250/458.1 |
| 2001/0045523 A1 | 11/2001 | Baer | |
| 2001/0045529 A1 | 11/2001 | Iketaki et al. | |
| 2002/0109101 A1 | 8/2002 | Hoffmann | |
| 2005/0162654 A1 | 7/2005 | Opsal et al. | |
| 2007/0023686 A1 * | 2/2007 | Wolleschensky et al. | 250/458.1 |
| 2007/0291353 A1 | 12/2007 | Iketaki et al. | |

FOREIGN PATENT DOCUMENTS

| | | |
|---|---|---|
| DE | 43 31 570 A1 | 3/1995 |
| DE | 199 56 620 A1 | 5/2001 |
| DE | 101 54 699 A1 | 5/2003 |
| DE | 102 31 543 B3 | 2/2004 |
| DE | 103 40 965 A1 | 3/2005 |
| EP | 1 584 918 A2 | 10/2005 |
| WO | WO 2005/029149 A1 | 3/2005 |
| WO | WO 2006/016475 A1 | 2/2006 |

* cited by examiner

*Primary Examiner* — Kiho Kim
(74) *Attorney, Agent, or Firm* — Duane Morris LLP (57) ABSTRACT

The invention is directed to a resolution-enhanced luminescence microscopy method in which a sample is excited to the emission of luminescence radiation through irradiation by excitation radiation, and an image of the luminescing sample is acquired. A first partial volume of the sample is irradiated by a first laser radiation field of the excitation radiation, and a second partial volume of the sample is irradiated by a second laser radiation field of the excitation radiation. The first partial volume of the sample and the second partial volume of the sample overlap one another partially but not completely. Only the first laser radiation field is modulated with a first frequency, and luminescence radiation is detected from the first partial volume of the sample with modulation filtering so that luminescence radiation from the second partial volume of the sample is suppressed.

16 Claims, 4 Drawing Sheets

LUMINESCENCE MICROSCOPY WITH ENHANCED RESOLUTION

RELATED APPLICATIONS

The present application is a continuation of U.S. National Stage application Ser. No. 12/442,093 filed on Mar. 19, 2009 of International PCT Application No. PCT/EP2007/007882 filed on Sep. 10, 2007, which claims benefit of German Application No. DE 10 2006 046 369.2 filed on Sep. 29, 2006, the contents of each are incorporated by reference in their entirety.

FIELD OF THE INVENTION

The invention is directed to resolution-enhanced luminescence microscopy and particularly to a method in which a luminescing sample to be examined is illuminated by excitation radiation and an image of the sample that has been excited to luminescence is obtained. The invention is further directed to a microscope for resolution-enhanced luminescence microscopy of a sample, means for exciting luminescence which irradiate the sample with excitation radiation, and means for acquiring an image of the excited sample.

BACKGROUND OF THE INVENTION

Luminescence microscopy is a typical field of application of light microscopy for examining biological samples. For this purpose, certain dyes (phosphors or fluorophores, as they are called) are used for specific tagging of samples, e.g., of cell parts. As mentioned, the sample is illuminated by excitation radiation and the luminescent light that is excited in this way is acquired by suitable detectors. For this purpose, the light microscope is usually provided with a dichroic beamsplitter combined with blocking filters which split off the fluorescence radiation from the excitation radiation and enable separate observation. This procedure makes it possible to display individual, differently colored cell parts in the light microscope. Naturally, more than one part of a specimen may also be dyed simultaneously with different dyes attaching themselves specifically to different structures of the specimen. This process is known as multiple luminescence. Samples which luminesce, per se, that is, without the addition of dye, can also be measured.

In the present context, and as a general rule, luminescence is used as an umbrella term for phosphorescence and fluorescence and embraces both processes.

Further, it is known to use laser scanning microscopes (LSM) for the examination of samples which shows only those planes situated in the focal plane of the objective in a three-dimensionally illuminated image by means of a confocal detection arrangement (called a confocal LSM in this case) or a nonlinear sample interaction (called multiphoton microscopy). An optical section is acquired and the recording of a plurality of optical sections at different depths of the sample then makes it possible by means of a suitable data processing device to generate a three-dimensional image of the sample which is composed of the different optical sections. Accordingly, laser scanning microscopy is suitable for examining thick specimens.

Naturally, a combination of luminescence microscopy and laser scanning microscopy in which a luminescing sample is imaged at different depth planes by means of a LSM is also used.

In principle, the optical resolution of a light microscope and of a LSM is diffraction-limited by physical laws. Special illumination configurations such as the 4Pi arrangement or arrangements with standing wave fields are known for optimal resolution within these limits. In this way, the resolution can be appreciably improved over a conventional LSM particularly in axial direction. Further, the resolution can be increased by up to a factor of 10 over a diffraction-limited confocal LSM by means of nonlinear depopulation processes.

In recent years, a number of such techniques have been proposed or developed which allow optical microscopy, particularly with LSM, to operate with a resolution beyond the conventional Abbe diffraction barrier [see Y. Garini, B. J. Vermolen and I. T. Young, "From micro to nano: recent advances in high-resolution microscopy", Curr. Opin. Biotechnol. 16, 3-12 (2005)]. In this connection, there is a basic distinction between nearfield and farfield methods, the latter being especially relevant because of their applicability to three-dimensional imaging in the field of biomedicine.

In conventional fluorescence microscopy with a given numerical aperture (NA) and excitation wavelength, the above-mentioned nonlinear relationship between the intensity of the exciting light and that of the emitted light must be produced in order to break the Abbe barrier of transmissible spatial frequencies in a significant way [see R. Heintzmann, T. M. Jovin and C. Cremer, "Saturated patterned excitation microscopy—a concept for optical resolution improvement", JOSA A 19, 1599-1609 (2002)]. This is achieved, for example, by means of multiphoton microscopy [see W. Denk, J. H. Strickler and W. W. Webb, "Two-photon fluorescence scanning microscopy, a concept for breaking the diffraction resolution limit", Science 248, 73-76 (1990)].

Other approaches include the methods of ground state depletion (GSD) [see U.S. Pat. No. 5,866,911 or S. W. Hell and M. Kroug, "Ground-state-depletion fluorescence microscopy: a concept for breaking the diffraction resolution limit", Appl. Phys. B 60, 495-497 (1995)] or stimulated emission depletion (STED) by Hell et al. [see DE 4416558 C2 S. W. Hell and J. Wichmann, "Breaking the diffraction resolution limit by stimulated emission; stimulated-emission-depletion fluorescence microscopy", Opt. Lett. 19, 780-782 (1994); T. A. Klar, E. Engel and S. W. Hell, "Breaking Abbe's diffraction resolution limit in fluorescence microscopy with stimulated emission depletion beams of various shapes", Phys. Rev. E 64, 066613 (2001); V. Westphal and S. W. Hell, "Nanoscale Resolution in the focal plane of an optical microscope", PRL 94, 143903 (2005)]. The common principle is based on the use of a distribution of excitation intensity and of saturation intensity in the sample, each of which is structured in such a way that the maximum of the former coincides with an interference minimum of the latter. A saturated excitation of the triplet state (hereinafter: GSD) or a saturated de-excitation of the fluorescing state (hereinafter: STED) makes it possible to deliberately quench the fluorescence of molecules which are not located in the immediate vicinity of the interference minimum. The radiation then proceeds only from the interference minimum. The up-conversion fluorescence depletion technique established by Iketaki et al. functions in a similar way [see T. Watanabe, Y. Iketaki, T. Omatsu, K. Yamamoto, M. Sakai and M. Fujii, "Two-point separation in super-resolution fluorescence microscope based on up-conversion fluorescence depletion technique", Opt. Exp. 24, 3271-3276 (2003)].

DE 19908883 A1 proposes a direct saturation of the fluorescence transition as a nonlinear process. The enhanced resolution is based on a periodically structured illumination of the sample so that there is a transfer of high object space frequencies in the range of the optical transfer function of the microscope. The transfer can be achieved through costly post-processing of data by computer.

SUMMARY OF THE INVENTION

Therefore, it is an object of the invention to provide a luminescence microscopy method and a luminescence microscope by which enhanced resolution is achieved without resorting to a plurality of wavelengths or costly postprocessing of data by computer.

This object is met according to the invention by a resolution-enhanced luminescence microscopy method in which a sample is excited to emission of luminescence radiation by irradiation with excitation radiation and an image of the luminescing sample is acquired, wherein a first partial volume of the sample is irradiated by a first laser radiation field of the excitation radiation and a second partial volume of the sample is irradiated by a second laser radiation field of the excitation radiation, wherein the first partial volume of the sample and the second partial volume of the sample overlap partially but not completely, only the first laser radiation field is modulated with a first frequency, and luminescence radiation is detected from the first partial volume of the sample with modulation filtering so that luminescence radiation from the second partial volume of the sample is suppressed.

The above-stated object is further met though a resolution-enhanced luminescence microscope with means for irradiating a sample with excitation radiation for exciting the emission of luminescence radiation and means for acquiring images of the luminescing sample, wherein the means for irradiating with excitation radiation have means for irradiating a first partial volume of the sample with a first laser radiation field and means for irradiating a second partial volume of the sample with a second laser radiation field, wherein the first partial volume of the sample and the second partial volume of the sample overlap one another partially but not completely, the means for irradiating the sample with the first laser radiation field have a modulator which modulates the first laser radiation field with a first frequency, and the means for acquiring images detect luminescence radiation from the first partial volume of the sample with modulation filtering so that the luminescence radiation from the second partial volume of the sample is suppressed by the filtering.

Like GSD or STED, the method according to the invention and the corresponding arrangement are single-point techniques in which resolution is enhanced beyond the resolution of the laser radiation field irradiation by the nonlinear cooperation of at least two laser radiation fields. Similar to DE 19908883 A1, direct saturation of the fluorescence transition can be applied as a nonlinear process. But simultaneous occupation of the triplet state no longer necessarily has negative results. It is essential that the fluorescence generated by the excitation laser and the fluorescence generated by the saturation laser are separated from one another by modulation marking (MMF: Modulation Marked Fluorescence) and suitable frequency-sensitive and/or phase-sensitive detection.

Accordingly, two laser radiation fields are radiated in according to the invention for increasing resolution. One of these two laser radiation fields is modulated. This laser radiation field is referred to hereinafter as center beam, center radiation or center laser radiation. A second laser radiation field whose radiation is not linearly modulated is radiated in so as to overlap this first laser radiation field but not completely cover it. This second laser radiation field will be referred to hereinafter as the side laser radiation or side laser beam. The two laser radiation fields are preferably structured in such a way that the maximum of the center laser beam coincides with the interference minimum of the side laser beam. In principle, the resolution is improved over the resolution at which the center laser beam and side laser beam are coupled in.

The approach according to the invention is a further development of the known GSD and STED methods. However, it has some advantages over these methods which will be described briefly:

GSD is based on a saturation of the triplet state and therefore requires molecules with a high rate of intersystem crossing. There is no such limitation in modulation-marked fluorescence because neither the side laser beam $T_{1,0}$ excitation nor the side laser beam $S_{1,0}$ excitation has an effect on the signal generated by the center laser beam. In the former case, there is no fluorescence, whereas in the latter case no modulated fluorescence occurs.

A drawback of the GSD method is the relatively long pixel dwell time required during scanning for image generation. In the first place, this is necessary to achieve the stationary equilibrium needed for triplet saturation (approximately 10 µs). In the second place, an initial relaxation of all molecules back into the ground state is required following the detection of a point for detecting the adjacent point (again approximately 10 µs). According to the invention, a saturation of the triplet state is not necessary, so that shorter dwell times can be used whose bottom limits are basically determined by the periods of the center laser beam modulations.

The intensities required within the framework of the invention are lower than those in STED.

A substantial advantage of the invention is the flexibility in the choice of dye. While the intersystem crossing required in GSD is limiting, the STED method requires molecules which allow the most efficient possible de-excitation of the $S_{1,0}$ state. By contrast, the invention makes it possible to use almost any dye whose level diagram corresponds approximately to that shown in FIG. 1. Optimization of the reaction rates (e.g., with respect to moderately longer fluorescence lifetimes) is advantageous, but does not present a fundamental limitation of the method. It must be emphasized that the essential modification with respect to conventional techniques is to be found more in the type of excitation and detection than in the choice of the sample to be examined (in stark contrast to DE 10325460 A1, for example).

In the STED experiments realized up to the present, two wavelengths are required, whereas the invention works with only one wavelength. It is not necessary to use a plurality of dichroic beamsplitters. Accordingly, a relatively simple construction can be used.

In STED experiments, it generally makes sense to use intensive pulsed lasers because the population of the excited state should be decreased in the side laser beam area before fluorescence takes place. In contrast, the invention can work with cw lasers irradiating simultaneously. However, it is advantageous to delay the irradiation by the center laser beam with respect to the side laser beam by approximately 10 ns because an extensive depopulation of the ground state has already taken place by then (see FIG. 7). In some circumstances, it is also possible to realize the modulation in the form of a pulsed laser.

The modulation-marked fluorescence (MMF) according to the invention makes it possible to improve high-resolution optical imaging to an even greater degree. It presents an alternative to the two single-point methods GSD and STED which are already known. As in these known methods, the method according to the invention also works with at least two laser radiation fields (center laser beam and side laser beam). However, whereas the aim in GSD and STED is to completely suppress the fluorescence in the side laser beam area, in MMF the center sample area and the laterally excited sample area are distinguished, e.g., by modulated center laser beam excitation followed by phase-sensitive detection of the signal of interest, and can therefore be separated. The use of a modulation-frequency-sensitive detection, e.g., by means of lock-in technology, is a central aspect for this purpose. Marked fluorescence in the side laser beam area, i.e., excitation through photons of the center laser radiation field, can be avoided by means of an unbalanced intensity ratio between the laser radiation fields and a saturated depopulation of the ground state. A substantial advantage of MMF over the known methods of GSD and STED is the freedom of choosing the fluorophor and the possibility of operating the center laser and side lasers at the same wavelength.

BRIEF DESCRIPTION OF THE DRAWINGS

The invention is described more fully by way of example in the following with reference to the drawings.

DESCRIPTION OF THE INVENTION

Figure 1:
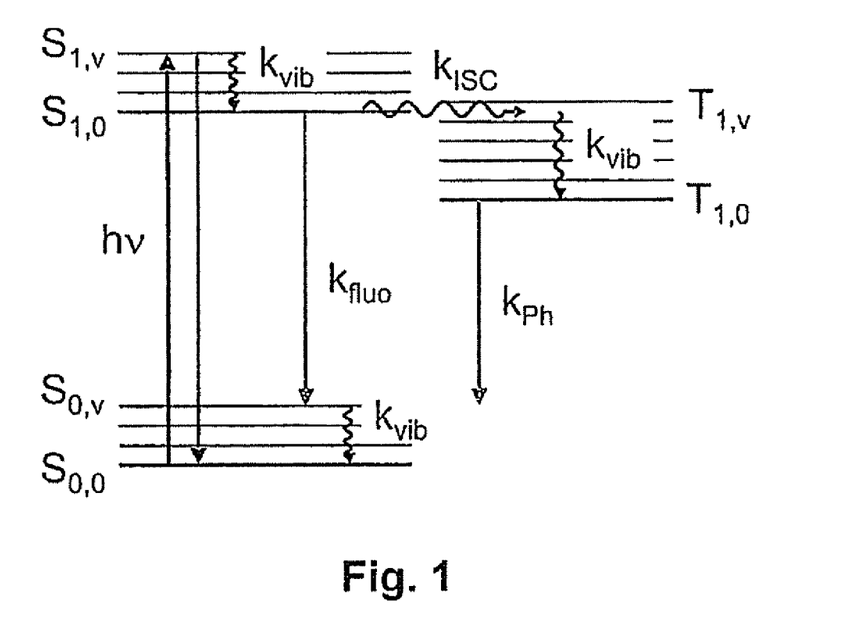
FIG. 1 shows, by way of example, an energy diagram of a dye molecule or of a sample which is used within the framework of the invention.

The typical arrangement, known per se, of the lowest energy level for a fluorescing dye molecule is shown schematically in FIG. 1. Usually photons of energy In excite the molecules from state $S_{0,0}$ (approximate vibrational ground state in the lowest electronic state) to a vibration-excited vibronic state $S_{1,\upsilon}$. Conversely, stimulated emission is, of course, also possible. Starting from $S_{1,\upsilon}$, a fast vibrational relaxation takes place in state $S_{1,0}$ and subsequently, as competing processes, either fluorescence or the transition to the triplet state $T_{i,\upsilon}$ with subsequent phosphorescence.

The excitation is carried out, according to the invention, by at least two different light fields which are arranged in the same way as the excitation laser radiation field and the saturation laser radiation field in the known GSD or STED method. The use of lasers seems sensible but generally does not represent a limitation of the method.

Figure 2:
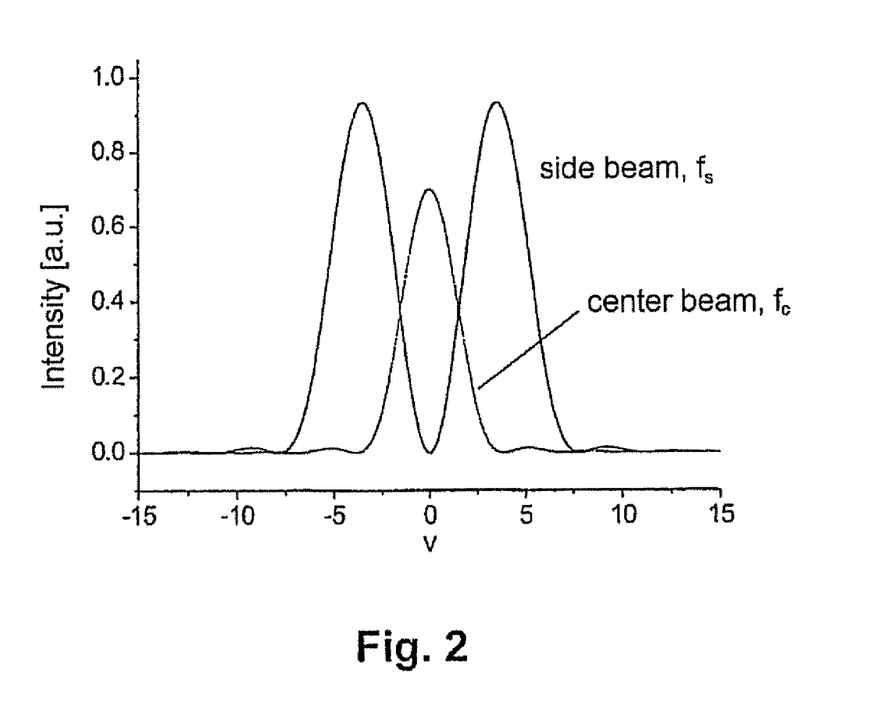
FIG. 2 shows a possible intensity distribution for a side beam and a center beam in the method according to the invention and in the device according to the invention.

FIG. 2 shows possible Airy intensity distributions of the laser radiation fields along the normalized coordinate v=kr*N.A. (where NA is the aperture, k is the wave number $2\pi/\lambda$, and r is the radial distance from the center). The fields are designated in the following as center beam and side beam. They can have the same wavelength.

Figure 3:
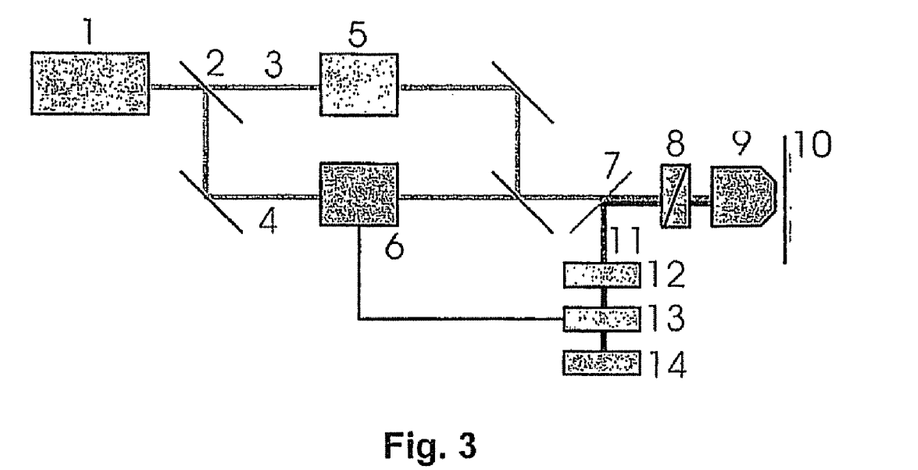
FIG. 3 shows, by way of example, a schematic for a device according to the invention.

FIG. 3 shows an embodiment form of the device which in this case is constructed similar to a Mach-Zehnder. A beamsplitter 2 divides the light into a center beam path 4 and a side beam path 3 after a light source 1. A unit for spatial beam shaping 5 is located in the side beam path 3. This unit can comprise, e.g., an annular aperture which is imaged on the sample 10. Other possibilities are described, for example, in T. A. Klar, E. Engel and S. W. Hell, "Breaking Abbe's diffraction resolution limit in fluorescence microscopy with stimulated emission depletion beams of various shapes", Phys. Rev. E 64, 066613 (2001). Of course, two separate beam sources can also be used.

A modulation unit 6 is provided for the center beam path 4, which is not subjected to spatial beam shaping, and modulates this beam with a frequency $f_c$. After overlapping, the two beams are focused in the sample 10 in a diffraction-limited manner. An objective 9 is used for this purpose. In addition, the focus is displaced in two dimensions by a scan unit 8.

Consequently, the overlapping of the center beam and side beam shown in FIG. 2 takes place at different locations in the sample 10. The fluorescence excited in this way is recorded by a detector 12, e.g., a confocal detector, via the objective 9, scan unit 8 and a preferably dichroic beamsplitter 7. A control unit (not shown) controls the operation of the device.

It is crucial that the fluorescence signal measured in this way can be associated with the respective beam 3, 4 by taking into account the modulation, i.e., the fluorescence is marked correspondingly. This is achieved by making use of modulation effects. In the simplest case, the side beam, for example, is not modulated ($f_s$=0), while the intensity of the center beam varies sinusoidally with a frequency $f_c$ typically from 1-100 MHz, for which purpose the modulation unit 6 is introduced in the center beam path. The fluorescence signal generated by the center beam is then likewise modulated with the frequency $f_c$. This effect corresponds among others to that which is also applied in the phase method for measuring fluorescence lifetimes (see, e.g., M. J. Booth and T. Wilson, "Low-cost, frequency-domain, fluorescence lifetime confocal microscopy", J. Microscopy 214, 36 (2004)). Alternatively, the side beam and center beam are each modulated with frequencies $f_s$ and $f_c$, where $f_s \neq f_c$.

The modulation frequency $f_c$ can be optimized in accordance with the dye. When detection is carried out in a phase-sensitive manner by means of a lock-in amplifier (13) at frequency $f_c$ as is shown by way of example in FIG. 3, the fluorescence signal generated by the center beam is extracted. Molecules which, in contrast, are excited (also) by the side laser beam show a non-modulated fluorescence and therefore do not contribute to the signal at the output 14. In order to further strengthen this effect, a polarization-sensitive detection can also take place making use of the fluorescence polarization.

In an arrangement corresponding to FIGS. 2 and 3, a resolution in the molecular range can be achieved when it is ensured that the probability that molecules located in a sample area in which the side laser has an intensity other than zero will be excited by the side laser beam is as high as possible. In this connection, it does not matter whether the state excited by the side laser beam has singlet characteristics or triplet characteristics. It is important only that the intensity of the radiation emitted by the molecules excited by the side laser beam is not modulated with frequency $f_s$ and is therefore suppressed by the lock-in method. The lock-in technique is, of course, only one example of a phase-sensitive or frequency-sensitive detection method.

Figure 4:
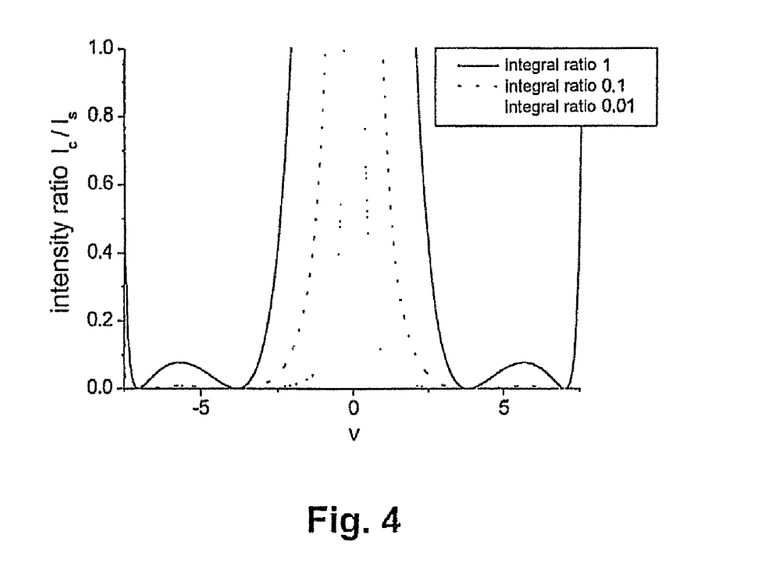
FIG. 4 shows the intensity ratio between the center beam and side beam for different embodiment forms of the invention.

The above-mentioned condition can be met, for example, when the side laser beam 5 has an intensity of sufficient magnitude that a saturation of the fluorescence transition occurs in the sample 10. In case of a two-level system $S_{0,0}$/$S_{1,\upsilon}$ as in FIG. 1, in which there are no vibrational states or triplet states and the fluorescence is stimulated or takes place spontaneously proceeding from $S_{1,\upsilon}$, the population $N_{1,\upsilon}$=1-$N_{0,0}$ of the $S_{1,\upsilon}$ state in stationary equilibrium is expressed by:

$$N_{1,v} \propto \frac{N_{p,s}}{2N_{p,s} + \frac{k_{fluo}}{\sigma}},$$

where $N_{p,s}$ is the photon flux (of the side laser beam 5) and $\sigma$ is the absorption cross section of the optical transfer. The intensity of the fluorescence radiation is proportional to $N_{1,\upsilon}$, by which the nonlinear relationship between the intensity of the exciting light and that of the emitted light which was mentioned above as necessary for high resolution can be directly verified. For very high photon fluxes, equal occupation of the states and, therefore, saturation is achieved. Further, when the intensity of the modulated center laser beam 4 is very much smaller compared to the side laser beam 5 (i.e., $N_{p,s} \gg N_{p,c}$), the probability of fluorescence excitation by the center laser beam 4 differs substantially from zero only at the interference minimum. This state of affairs is shown clearly in FIG. 4, where the ratio $I_c/I_s$ (center beam intensity to side beam intensity) is plotted as a function of the normalized coordinate v corresponding to the intensity curves shown in FIG. 2. Three different ratios of the respective integral intensities are taken into account. It will be seen that there is only a very low probability of excitation by the center laser beam 5 with an integral ratio of 0.01 (i.e., the side laser beam 4 is 100 times stronger than the center laser beam 5) in the range of |v|>1. In this case, localized molecules correspondingly show hardly any modulated fluorescence and are consequently suppressed during modulation-frequency-sensitive detection. This mechanism accordingly achieves an increase in resolution beyond the diffraction boundary.

Figure 5:
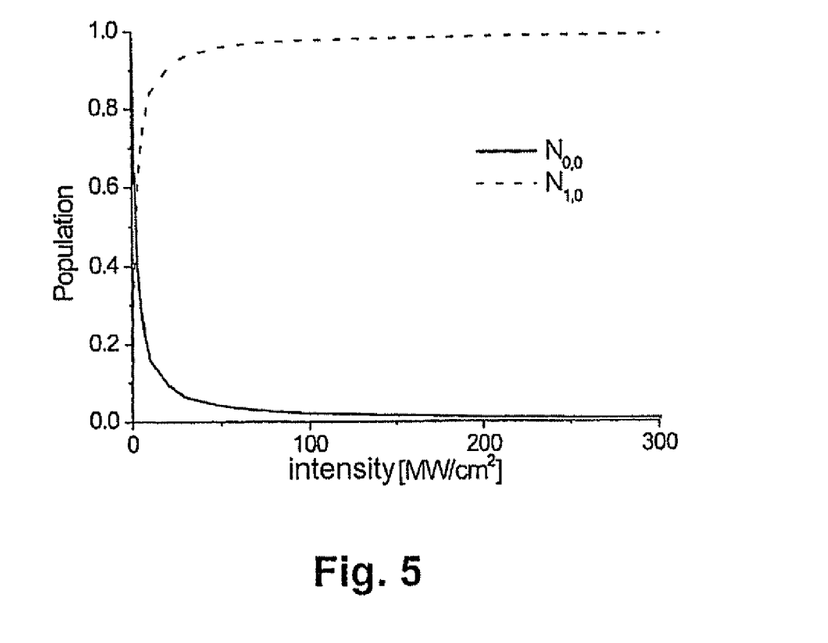
FIG. 5 shows the equilibrium population as a function of the radiated laser beam intensity for a dye that can be used, for example, within the framework of the invention.

In a further development, the vibration levels of the individual electronic states shown in FIG. 1 are included in the overlapping. The triplet state will continue to be left out of consideration for the time being ($k_{ISC}$=0). In order to determine occupation of the individual states during irradiation by the side laser beam 4, rate equations can be solved for different laser intensities in a first approximation (leaving aside coherence terms). FIG. 5 shows the population of states $S_{0,0}$ and $S_{1,0}$ ($N_{0,0}$ and $N_{1,0}$, respectively) as a function of the laser beam intensity. By way of example, an absorption cross section of $s=10^{-16}$ cm$^{-2}$, a vibrational relaxation rate of $k_{vib}=(10^{-12}$ s)$^{-1}$ and a fluorescence rate of $k_{fluo}=(2*10^{-9}$ s)$^{-1}$ were recorded. Values were shown for the stationary equilibrium which is always achieved after an illumination period of about 10 ns. The sum of all of the populations is scaled to 1. It will be seen that the ground state for intensities greater than 100 MW/cm$^2$ is almost completely depopulated. Further, the curves shown in FIG. 6 can be derived from the $N_{0,0}$ curve shown in FIG. 5 and demonstrate the depopulation of the ground state generated by the side laser beam as a function of coordinate v. An intensity profile corresponding to FIG. 2 with three different peak intensity values (intensity at maximum: 2 MW/cm$^2$, 20 MW/cm$^2$, 200 MW/cm$^2$) was assumed. A saturation effect leading to a constriction of the ground state population can be seen clearly at the interference minimum. Now, if, in addition, the modulated center laser is radiated in at a low intensity, the modulated excitation is substantially limited to the range of v=0. In this case, there is an interplay between the depopulation effect and the above-mentioned circumstances of the different excitation probabilities (FIG. 4).

Figure 6:
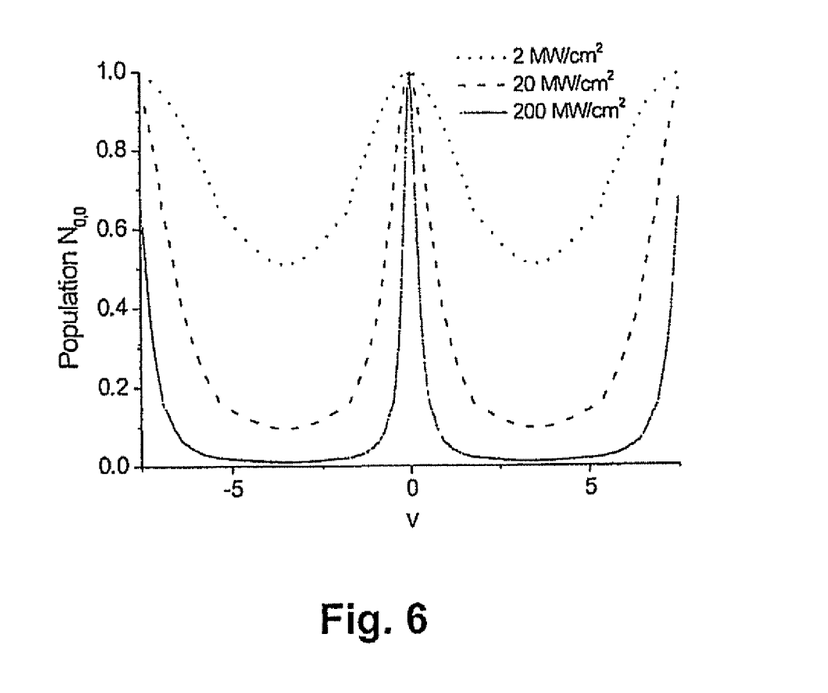
FIG. 6 shows the equilibrium population of the ground state along a normalized coordinate during irradiation by the side laser beam in the method according to the invention for three different possible peak intensities.
Figure 7:
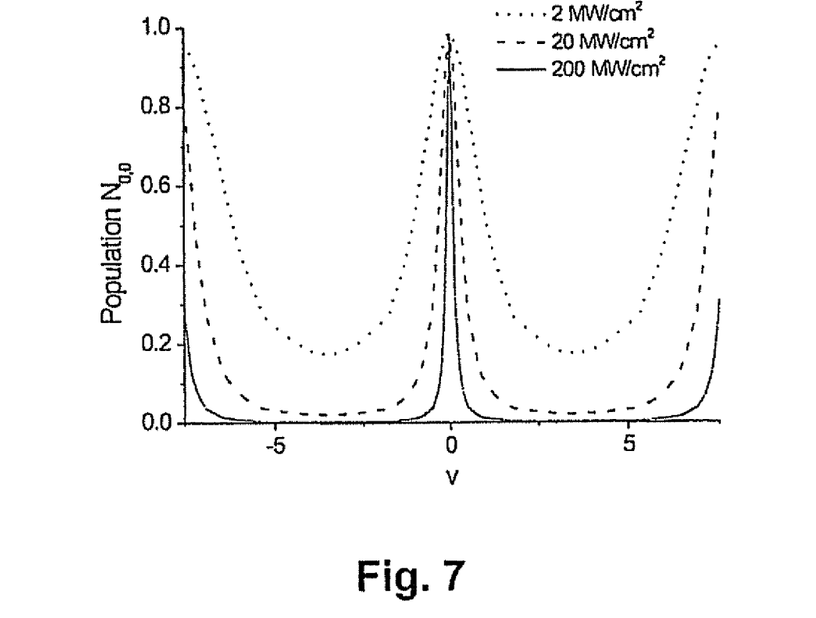
FIG. 7 shows a diagram similar to that shown in FIG. 6 for other dye parameters.

Naturally, the specific shape of the curves in FIG. 6 depends among other things on the properties of the selected fluorophor or sample 10. The example above is based on a fluorescence lifetime of 2 ns. A more efficient saturation (and, therefore, lower intensities) can be realized by using dyes with longer lifetimes. FIG. 7 corresponds to FIG. 6 and assumes a lifetime of 10 ns. It can clearly be seen that a flattening of the population curve occurs already at 20 MW/cm$^2$.

Figure 8:
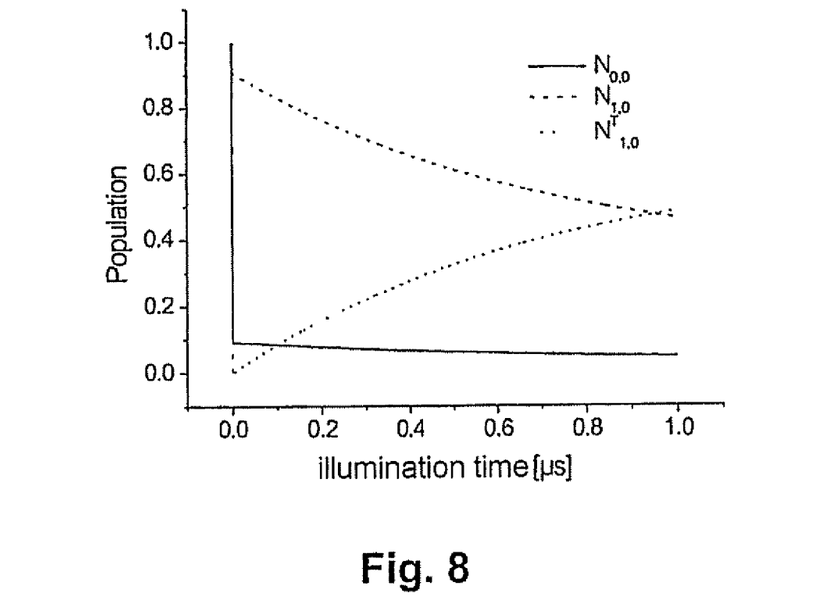
FIG. 8 shows the population of the ground states and excited states as a function of the illumination period in a particular embodiment form of the invention.

In a real system, the condition of a vanishing intersystem crossing is generally not entirely met. In this connection, typical rates of $K_m=(10^{-6}$ s)$^{-1}$ and $k_{Ph}=(2*10^{-6}$ s)$^{-1}$ are assumed such as those documented for rhodamine 6G (see M. Heupel, "Fluoreszenzspektroskopie als neue Messmethode zur höchstempfindlichen Untersuchung transienter Zustände", dissertation, Uni-Siegen (2001)). FIG. 8 shows how the populations of states $S_{0,0}$, $S_{1,0}$ and $T_{1,0}$ (see FIG. 1) change within 1 μs under these conditions assuming an irradiation intensity of 20 MW/cm$^2$. Roughly this illumination period is necessary in order to detect a modulation in the range of several tens of MHz. It will be seen that the lowest excited singlet state and the triplet state are occupied approximately equally at the selected parameters during the time period shown here. In stationary equilibrium, the occupation shifts in favor of the triplet state, whose population in this example is approximately twice as high. In this case, the ground state is extensively depopulated. The extent of the depopulation often depends less on the illumination period than on the laser intensity that is used. When using a side laser beam profile as shown in FIG. 2, a saturation effect similar to that in FIG. 6 or 7 results again. Since the occupation of the triplet state is often linked with a photobleaching process by singlet oxygen (see C. Eggeling, A. Vollmer and C. A. M. Seidel, "Molecular Photobleaching kinetics of Rhodamine 6G under the conditions of one- and two-photon induced confocal fluorescence microscopy", ChemPhysChem 6, 791-804 (2005)), a rather short exposure period seems to be advantageous. However, it must be ensured that the modulations of the center laser beam 5 remain detectable, i.e., a sufficient quantity of fluorescence cycles is required.

It should be mentioned that laser radiation field arrangements and modulation schemes other than those described above are also conceivable. For example, the fluorescence of molecules can be detected in the area of overlap between two laser radiation fields by applying lock-in detection with the sum frequency or difference frequency $f_s+f_c$ or $f_s-f_c$, respectively (in this case, the designations center field and side field may no longer apply under certain circumstances). When two simple (partially overlapping) Airy profiles are selected, a resolution similar to that in point spread autocorrelation function imaging can be achieved [see G. J. Brakenhoff and M. Müller, "Improved axial resolution by point spread autocorrelation function imaging", Opt. Lett. 21, 1721-1723 (1996)].

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

The invention claimed is:

1. A method for resolution-enhanced luminescence microscopy comprising exciting a sample to the emission of luminescence radiation through irradiation by excitation radiation, and acquiring an image of the luminescing sample,
   wherein a first partial volume of said sample is irradiated by a first laser radiation field of the excitation radiation, and a second partial volume of said sample is irradiated by a second laser radiation field of the excitation radiation, such that both partial volumes emit said luminescence radiation,
   wherein said first partial volume of said sample and said second partial volume of said sample overlap one another partially but not completely, resulting in the sample luminescing over both, the first and second partial volumes,
   wherein either only the first laser radiation field is modulated with a first frequency, or the first laser radiation field is modulated with a first frequency and the second laser radiation field is modulated with a second frequency being different to the first radiation frequency, thus making only the luminescence radiation emitted from the first partial volumes being modulated with the first frequency, and
   wherein the luminescence radiation of the sample is detected with modulation filtering so that the luminescence radiation from the second partial volume of the sample is suppressed and the luminescence radiation from the first partial volume is extracted from regions of the first partial volume which do not overlap with the second partial volume resulting in the resolution enhancement.

2. The method according to claim 1, wherein said second partial volume of said sample is brought to luminescence saturation by said second laser radiation field.

3. The method according to claim 1, wherein the intensity of said second laser radiation field is at least 50-times greater than that of the first laser radiation field.

4. The method according to claim 1, wherein the intensity of said second laser radiation field is at least 100-times greater than that of the first laser radiation field.

5. The method according to claim 1, wherein at least said first laser radiation field is focused on said sample in a diffraction-limited manner.

6. The method according to claim 1, wherein said second laser radiation field is modulated with a second frequency that differs from the first frequency.

7. The method according to claim 1, wherein modulation-filtering detection is carried out by lock-in technique.

8. The method according to claim 1, wherein the first frequency is between 1 MHz and 100 MHz.

9. A resolution-enhanced luminescence microscope comprising
   means for irradiating a sample with excitation radiation for exciting the emission of luminescence radiation,
   means for acquiring images of the luminescing sample,
   wherein the means for irradiating with excitation radiation have means for irradiating a first partial volume of the sample with a first laser radiation field and means for irradiating a second partial volume of the sample with a second laser radiation field, such that both partial volumes emit said luminescence radiation,
   wherein the first partial volume of the sample and the second partial volume of the sample overlap one another partially but not completely to excite emission of luminescence radiation over both, the first and the second partial volumes,
   said means for irradiating the sample with the first laser radiation field having a modulator which modulates either only the first laser radiation field with a first frequency or the first laser radiation field with a first frequency and the second laser radiation with a second frequency being different to the first radiation frequency, to make only the luminescence radiation emitted from the first partial volumes being modulated with the first frequency, and
   said means for acquiring images detect luminescence radiation from the said sample with modulation filtering so that the luminescence radiation from the second partial volume of the sample is suppressed by the filtering and the luminescence radiation from the first partial volume is extracted from regions of the first partial volume which do not overlap with the second partial volume resulting in the resolution enhancement.

10. The microscope according to claim 9, wherein said second partial volume of the sample is brought to luminescence saturation by the means for irradiating with the second laser radiation field (4).

11. The microscope according to claim 9, wherein the intensity of the second laser radiation field is at least 50-times greater than that of the first laser radiation field.

12. The microscope according to claim 9, wherein the intensity of the second laser radiation field is at least 100-times greater than that of the first laser radiation field.

13. The microscope according to claim 9, further comprising optics which focus the laser radiation for the first laser radiation field on the sample in a diffraction-limited manner.

14. The microscope according to according to claim 9, wherein a modulator is provided which modulates the second laser radiation field with a second frequency that differs from the first frequency.

15. The microscope according to claim 9, wherein said means for acquiring images have a lock-in amplifier, the first frequency and the signals of a detector being fed to the lock-in amplifier.

16. The microscope according to claim 9, wherein the first frequency is between 1 MHz and 100 MHz.

* * * * *

UNITED STATES PATENT AND TRADEMARK OFFICE
CERTIFICATE OF CORRECTION

PATENT NO. : 8,399,857 B2  
APPLICATION NO. : 13/342370  
DATED : March 19, 2013  
INVENTOR(S) : Helmut Lippert It is certified that error appears in the above-identified patent and that said Letters Patent is hereby corrected as shown below:

In the Specification

Column 5, line 50, now reads: "Usually photons of energy In excite the"
should read -- Usually photons of energy hʋ excite the --.

Column 8, line 17, now reads: "typical rates of $K_m = (10^{-6}\,s)^{-1}$ ..."
should read -- typical rates of $K_{ISC} = (10^{-6}\,s)^{-1}$ ... --.

Signed and Sealed this
Eleventh Day of March, 2014

Michelle K. Lee
*Deputy Director of the United States Patent and Trademark Office*